US005922866A

United States Patent [19]
Miyata et al.

[11] Patent Number: 5,922,866
[45] Date of Patent: Jul. 13, 1999

[54] PROCESS FOR PREPARING QUINAZOLIN-4-ONE DERIVATIVES

[75] Inventors: Kazuyoshi Miyata; Yasuhisa Kurogi; Yasuhiro Sakai; Yoshihiko Tsuda, all of Naruto, Japan

[73] Assignee: Otsuka Pharmaceutical Factory, Inc., Tokushima, Japan

[21] Appl. No.: 09/011,826

[22] PCT Filed: Aug. 26, 1996

[86] PCT No.: PCT/JP96/02388

§ 371 Date: Feb. 25, 1998

§ 102(e) Date: Feb. 25, 1998

[87] PCT Pub. No.: WO97/08153

PCT Pub. Date: Mar. 6, 1997

[30] Foreign Application Priority Data

Aug. 30, 1995 [JP] Japan .................................. 7-221518
Sep. 11, 1995 [JP] Japan .................................. 7-232146

[51] Int. Cl.⁶ .............................. C07F 9/32; C07F 9/40; C07D 239/91; C07D 239/96
[52] U.S. Cl. ........................... 544/244; 544/289; 544/290
[58] Field of Search ..................... 544/290, 289, 544/244

[56] References Cited

U.S. PATENT DOCUMENTS 3,966,731  6/1976  Inoue et al. ........................... 260/256.4
4,714,702  12/1987  Inoue et al. ............................. 514/259

OTHER PUBLICATIONS

Inoe et al., CA Acc No. 1986:109677, JP 60178817, 1985.
Ismail et al. CA Acc No. 114:23917, Indian J. Chem., 29B, 811–13, 1990.
Ismail et al. CA Acc No. 1992:151715, Polish J. Chem. 65, 1259–63, 1991.
Vaidya et al., "Unusual cyclization of amidine salts in the formation of quinazolones", J. Org. Chem.47, 1777–9, 1982.
Satoh et al., "Limitation of stunning in dog myocardium by nucleoside and nucleotide mixture, OG–VI", *Coronary Artery Disease*, 4:11:1007–1012, (1993).
Kan et al., "Protective effects of a nucleoside–nucleotide mixture on the hypoxic rat heart evaluated by in vivo phosporous–31 NMR spectroscopy", *Chemical Abstracts*, No. 248095, 116:25, (Jun. 22, 1992).
Eliseev et al., "Effect of guanosine 5'–monophosphate and inosine on isolated frog heart", *FIZIO. ZH. SSSR*, 72:6:763–766, (1986).
Woollard et al., "Inosine as a selective inotropic agent on ishaemic mycarium", *Cardiovasc. Res.,* 15:11:659–667, (1981).
Lukyanova et al., "A protective effect of guanosine–5'–monophosphate in adrenaline–induced heart failure", *Anesteziol. Reanimatol.,* 5:19–21, (1987).

Czarnecki et al., "Inosine—a natural modulator of contractility and myocardial blood flow in the ischemic heart?", *American Heart Journal,* 124:6:1446–1459, (1992).

(List continued on next page.)

*Primary Examiner*—Mark L. Berch
*Assistant Examiner*—Ann Razgunas
*Attorney, Agent, or Firm*—Sughrue, Mion, Zinn, Macpeak & Seas, PLLC

[57] ABSTRACT

The present invention provides a novel process for preparing a series of quinazolin-4-one derivatives in high yields with reduced amounts of byproducts, the process comprising reacting, in the presence of a base, a trialkylsilyl halide with a compound represented by the formula

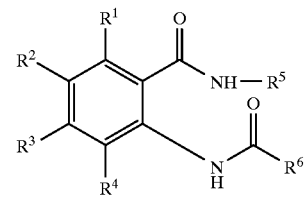

wherein; $R^5$ is a phenyl group which may have 1 to 3 substituents each selected from a lower alkyl group, a lower alkoxy group or a halogen atom, a lower alkyl group, a phenyl-lower alkyl group which may have a halogen atom as a substituent on the phenyl ring, a lower alkenyl group, a lower alkoxy-lower alkyl group or a lower alkynyl group; $R^6$ is a lower alkyl group, a halogen-substituted lower alkyl group, a lower alkoxycarbonyl group or a phenyl group which may have, as a substituent, a lower alkyl group or a group of the formula

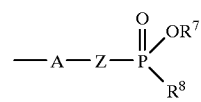

wherein A is an oxygen atom or a single bond, Z is a lower alkylene group, $R^7$ is a lower alkyl group and $R^8$ is a lower alkoxy group, a phenyl group or a phenyl-lower alkoxy group which may have a halogen atom on the phenyl ring;

to produce the quinazolin-4-one derivatives which is valuable as pharmaceuticals or intermediates for synthesis thereof and represented by the formula

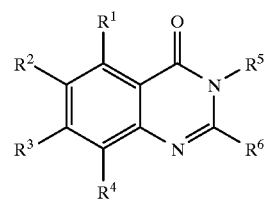

wherein $R^1, R^2, R^3, R^4, R^5$, and $R^6$ are as defined above.

8 Claims, No Drawings

OTHER PUBLICATIONS

Smiseth O.A., "Inosine infusion in dogs with acute ischemic left ventricular failure: favourable effects on myocardial performance and metabolism", *Cardiovasc. Res.,* 17:4:192–199, (1983).

Wyatt et al., "Purine–enriched asanguineous cardioplegia retards adenosine triphosphate degradation during ischemia and improves postischemic ventricular function", *J. Thorac. Cardiovasc. Surg.,* 97:5:771–778, (1989).

Takeo et al., "Adenine Nucleotide metabolites are beneficial for recovery of Cardia Contractile Force after Hypoxia", *J. Mol. Cell. Cardiol.,* 20:3:187–199, (1988).

Kypson et al., "Effects of Uridine on the Performance and the Metabolism on Oxygenated and Hypoxic Rabbit Hearts", *J. Mol. Cell. Cardiol.,* 10:545–565, (1978).

Harmsen et al., "Enhanced ATP and GTP synthesis from hypoxanthine or inosine after myocardial ischemia", *Am. J. Physiol.,* 246:15, (1984).

Czarnecki et al., "Haemodynamic effects of inosine. A new drug for failing human heart", *Pharmacological Research,* 21:5:587–594, (1989).

PROCESS FOR PREPARING QUINAZOLIN-4-ONE DERIVATIVES

TECHNICAL FIELD

The present invention relates to novel processes for preparing quinazolin-4-one derivatives, in particular quinazolin-4-one derivatives which are valuable as intermediates for synthesis of compounds for use in pharmaceuticals for diabetes, or which are useful by themselves as active ingredients of therapeutic agents for diabetes.

BACKGROUND ART

Conventionally, quinazolin-4-one derivatives are prepared, for example by the process disclosed in J. Org. Chem., 41 (10), 1763 (1976) which comprises heating a diamide derivative for cyclization. However, since the process employs a high heating temperature (250° C. or above), it produces the quinazolin-4-one derivative in a very low yield and generates large amounts of byproducts.

An object of the present invention is to provide a novel process for preparing a series of quinazolin-4-one derivatives useful as pharmaceuticals or intermediates for synthesis thereof in higher yields with reduced amounts of byproducts.

The present inventors carried out extensive research and found that the following process can achieve the above object. The present invention has been accomplished based on the finding.

DISCLOSURE OF INVENTION

The present invention provides a process for preparing a quinazolin-4-one derivative, the process comprising reacting, in the presence of a base, a trialkylsilyl halide with a compound represented by the formula (1)

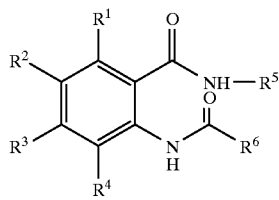

wherein $R^1$, $R^2$, $R^3$ and $R^4$ are the same or different and each represent a hydrogen atom, a lower alkyl group, a halogen atom, a nitro group, a lower alkoxy group, a cyano group, an N-lower alkylcarbamoyl group, a lower alkoxycarbonyl group or a halogen-substituted lower alkyl group, $R^5$ is a phenyl group which may have 1 to 3 substituents each selected from a lower alkyl group, a lower alkoxy group or a halogen atom, a lower alkyl group, a phenyl-lower alkyl group which may have a halogen atom as a substituent on the phenyl ring, a lower alkenyl group, a lower alkoxy-lower alkyl group or a lower alkynyl group; $R^6$ is a lower alkyl group, a halogen-substituted lower alkyl group, a lower alkoxycarbonyl group or a phenyl group which may have, as a substituent, a lower alkyl group or a group of the formula

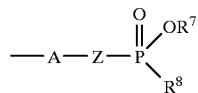

wherein A is an oxygen atom or a single bond, Z is a lower alkylene group, $R^7$ is a lower alkyl group and $R^8$ is a lower alkoxy group, a phenyl group or a phenyl-lower alkoxy group which may have a halogen atom on the phenyl ring; to produce quinazolin-4-one derivative represented by the formula (2)

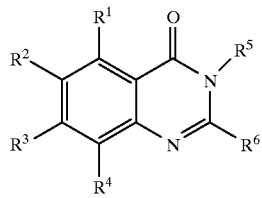

wherein $R^1$, $R^2$, $R^3$, $R^4$, $R^5$ and $R^6$ are as defined above.

More specifically, the present invention provides the processes as defined above wherein the base is a tertiary amine, wherein the trialkylsilyl halide is chlorotrialkylsilane, wherein the base and trialkylsilyl halide are used each in an amount of 3 to 20 equivalents, and wherein the reaction temperature is in the range of 0 to 100° C.

In the above formula representing the quinazolin-4-one derivative prepared by the process of the invention, the groups represented by $R^1$ to $R^6$ are as follows.

The halogen atom may be a fluorine, chlorine, bromine or iodine atom.

Examples of the lower alkoxy group include methoxy, ethoxy, propoxy, isopropoxy, butoxy, tert-butoxy, pentyloxy, hexyloxy and like groups.

Examples of the lower alkyl group include methyl, ethyl, propyl, isopropyl, butyl, tert-butyl, pentyl, hexyl and like groups.

Examples of the phenyl-lower alkyl group which may have a halogen atom as a substituent on the phenyl ring include benzyl, α-phenetyl, β-phenetyl, 1-phenylpropyl, 2-phenylpropyl, 3-phenylpropyl, 4-phenylbutyl, 5-phenylpentyl, 6-phenylhexyl, 2-bromobenzyl, 3-bromobenzyl, 4-bromobenzyl, 4-chlorobenzyl, 4-fluorobenzyl, 4-iodobenzyl, 2-bromo-4-fluorobenzyl, 2-fluoro-4-bromobenzyl, 2-chloro-4-fluorobenzyl, 2-fluoro-4-chlorobenzyl, 2-bromo-4-chlorobenzyl, 2-chloro-4-bromobenzyl, 2-iodo-4-bromobenzyl, 3-chloro-5-bromobenzyl, 3-bromo-5-fluorobenzyl, 3-chloro-5-fluorobenzyl, 3-iodo-5-bromobenzyl, 3-chloro-5-iodobenzyl and like groups.

Examples of the lower alkenyl group include vinyl, 1-methylvinyl, 1-propenyl, 2-propenyl, 1-butenyl, 2-butenyl, 3-butenyl, 2,2-dimethylvinyl, 1-pentenyl, 2-pentenyl, 3-pentenyl, 4-pentenyl, 1-hexenyl, 2-hexenyl, 3-hexenyl, 4-hexenyl, 5-hexenyl and like groups.

Examples of the halogen-substituted lower alkyl group include trifluoromethyl, pentafluoroethyl, heptafluoropropyl, nonafluorobutyl, undecafluoropentyl, tridecafluorohexyl, chloromethyl, bromomethyl, iodomethyl, 2-chloroethyl, 3-chloropropyl, 4-chlorobutyl, 5-chloropentyl, 6-chlorohexyl and like groups.

Examples of the lower alkoxy-lower alkyl group include methoxymethyl, ethoxymethyl, propoxymethyl, butoxymethyl, pentyloxymethyl, hexyloxymethyl, 2-methoxyethyl, 3-methoxypropyl, 4-methoxybutyl, 5-methoxypentyl, 6-methoxyhexyl and like groups.

Examples of the lower alkynyl group include ethynyl, 2-propynyl, 3-butynyl, 4-pentynyl, 5-hexynyl and like groups.

Examples of the phenyl-lower alkoxy group which may have a halogen atom on the phenyl ring include benzyloxy, 2-phenylethoxy, 3-phenylpropoxy, 4-phenylbutoxy, 5-phenylpentyloxy, 6-phenylhexyloxy, 4-chlorobenzyloxy, 3-chlorobenzyloxy, 2-chlorobenzyloxy, 4-bromobenzyloxy and like groups.

Examples of the lower alkylene group include methylene, ethylene trimethylene, tetramethylene, pentamethylene, hexamethylene and like groups.

Examples of the N-alkylcarbamoyl group include N-methylcarbamoyl, N-ethylcarbamoyl, N-propylcarbamoyl, N-butylcarbamoyl, N-pentylcarbamoyl, N-hexylcarbamoyl and like groups.

Examples of the lower alkoxycarbonyl group include methoxycarbonyl, ethoxycarbonyl, propoxycarbonyl, butoxycarbonyl, pentyloxycarbonyl, hexyloxycarbonyl and like groups.

Examples of the lower alkanoyloxy group include acetoxy, propionyloxy, butyryloxy, valeryloxy, pivaloyloxy, hexanoyloxy, heptanoyloxy and like groups.

Examples of the phenyl group which may have 1 to 3 substituents each selected from a lower alkyl group, a lower alkoxy group or a halogen atom include phenyl, 2-methylphenyl, 3-methylphenyl, 4-methylphenyl, 4-ethylphenyl, 4-propylphenyl, 4-butylphenyl, 4-pentylphenyl, 4-hexylphenyl, 2, 3-dimethylphenyl, 2,4-dimethylphenyl, 3,4-dimethylphenyl, 3,4,5-trimethylphenyl, 2-chlorophenyl, 3-chlorophenyl, 4-chlorophenyl, 4-bromophenyl, 4-iodophenyl, 4-fluorophenyl, 2,4-dichlorophenyl, 2,4,6-trichlorophenyl, 2-methoxyphenyl, 3-methoxyphenyl, 4-methoxyphenyl, 4-ethoxyphenyl, 4-propoxyphenyl, 4-butoxyphenyl, 4-pentyloxyphenyl, 4-hexyloxyphenyl, 2,3-dimethoxyphenyl, 2,4-dimethoxyphenyl, 3,4-dimethoxyphenyl, 3,4,5-trimethoxyphenyl, 4-chloro-2-methylphenyl, 2-chloro-4-methylphenyl, 4-methoxy-3-methylphenyl, 3-methoxy-4-methylphenyl, 4-chloro-2-methoxyphenyl, 2-chloro-4-methoxyphenyl, 3,5-di-t-butyl-4-methoxyphenyl and like groups.

Among the groups represented by $R^6$ the phenyl group which may have, as a substituent, a lower alkyl group or a group of the above formula may be, for example, phenyl, 2-methylphenyl, 3-methylphenyl, 4-methylphenyl, 4-ethylphenyl, 4-propylphenyl, 4-butylphenyl, 4-pentylphenyl, 4-hexylphenyl, 4-[(diethoxyphosphoryl)methyl]phenyl, 3- [(diethoxy-phosphorylmethyl]phenyl, 2-[(diethoxy-phosphoryl)methyl]-phenyl, 4-[(dimethoxyphosphoryl)-methyl]phenyl, 4-[(dipropoxyphosphoryl)methyl]phenyl, 4-[(diisopropoxyphosphoryl)methyl]phenyl, 4-[(dibutoxyphosphoryl)-methyl]phenyl, 4-[(pentyloxyphosphoryl)methyl]phenyl, 4-[(dihexyloxyphosphoryl)methyl]phenyl, 4-[2-(diethoxyphosphoryl)ethyl]phenyl, 4-[3-diethoxyphosphoryl)propyl]phenyl, 4-[4- (diethoxyphosphoryl)-butyl]phenyl, 4-[5-(diethoxyphosphoryl)pentyl]phenyl, 4-[6-(diethoxyphosphoryl)hexyl]phenyl, 4-[(ethoxyphenyl-phosphoryl)methyl]phenyl, 4-[(methoxyphenylphosphoryl)-methyl]phenyl, 4-[(phenylpropoxyphosphoryl)methyl]phenyl, 4-[(butoxyphenylphosphoryl)methyl]phenyl, 4-[(pentyloxy-phenylphosphoryl)methyl]phenyl, 4-[(hexyloxyphenyl-phosphoryl methyl]phenyl, 4-[(benzyloxyethoxyphosphoryl)-methyl]phenyl, 4-[[(4-chlorobenzyloxy)ethoxyphosphoryl]-methyl]phenyl, 4-[[(3-chlorobenzyloxy)ethoxyphosphoryl]-methyl]phenyl, 4-[[(2-chlorobenzyloxy)ethoxyphosphoryl]-methyl]phenyl, 4-[(diethoxyphosphoryl)methoxy]phenyl, 3-[(diethoxyphosphoryl)methoxy]phenyl, 2-[(diethoxy-phosphoryl)methoxy]phenyl, 4-[2-(diethoxyphosphoryl)-ethoxy]phenyl, 4-[3-(diethoxyphosphoryl)propoxy]phenyl, 4-[4-(diethoxyphosphoryl)butoxy]phenyl, 4-[5-(diethoxy-phosphoryl)pentyloxy]phenyl, 4-[6-(diethoxyphosphoryl)-hexyloxy]phenyl or like groups.

According to the process of the invention, the compound of the formula (1) (starting material) is cyclized by reacting a trialkylsilyl halide with the compound in an inert solvent in the presence of a base.

Usable inert solvents are, for example, aromatic or aliphatic hydrocarbons such as benzene, toluene, xylene and petroleum ether, ethers such as diethyl ether, hydrocarbon halides such as dichloromethane, chloroform, carbon tetrachloride and 1,2-dichloroethane, etc.

Preferably usable bases are, for example, tertiary amines such as triethylamine, N,N-diethylaniline N-methylmorphorine, pyridine and 4-dimethylaminopyridine.

Preferred examples of the trialkylsilyl halide include chlorotrialkylsilanes such as chlorotrimethylsilane, chlorotriethylsilane, chloroethyldimethylsilane, chlorodimethylpropylsilane, chlorobutyldimethylsilane, chlorotripropylsilane, tributylchlorosilane and chloroethylmethylpropylsilane.

The amounts of the trialkylsilyl halide and base are not restricted but it is generally suitable to use them each in an amount of 1 to excess equivalents, preferably 3 to 20 equivalents. The reaction is carried out usually at temperatures ranging from 0 to 100° C. and is completed in a period of about 0.5 to 20 hours.

The starting material for use in the invention can be obtained, for example, by the process illustrated by the following reaction scheme.

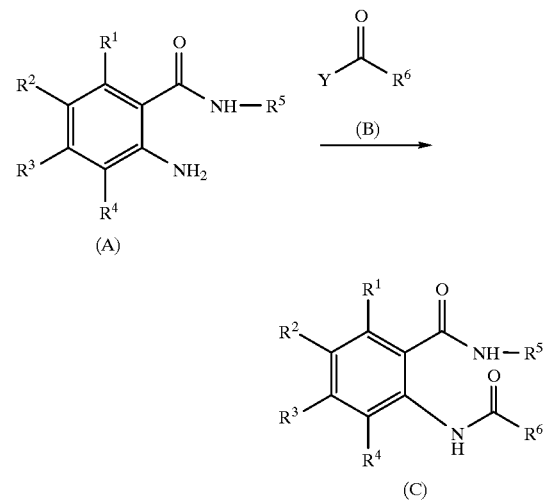

wherein $R^1$, $R^2$, $R^3$, $R^4$, $R^5$ and $R^6$ are as defined above, and Y is a halogen atom.

In the above reaction, the compound (A) is reacted with the acyl halide (B) in an inert solvent in the presence of a deacidifying agent. Usable inert solvents are, for example, aromatic or aliphatic hydrocarbons such as benzene, toluene, xylene and petroleum ether, ethers such as diethyl ether, ketones such as acetone, methyl ethyl ketone and acetophenone, hydrocarbon halides such as dichloromethane, chloroform, carbon tetrachloride and 1,2-dichloroethane, etc. Preferred examples of the deacidifying agent are amines such as triethylamine, N,N-diethylaniline, N-methylmorphorine, pyridine and 4-dimethylaminopyridine.

The acyl halide (B) is used preferably in an equimolar to small excess amount relative to the compound (A), and the deacidifying agent is used in an equimolar to excess amount relative to the compound (A). The reaction can be carried out generally at temperatures ranging from 0° C. to room temperature and is completed in a period of about 0.5 to 50 hours.

According to the invention, the contemplated quinazolin-4-one derivatives can be easily prepared in high yields. The obtained quinazolin-4-one derivatives are valuable as intermediates for synthesis of compounds for use in pharmaceuticals for diabetes, and useful by themselves as active ingredients of therapeutic agents for diabetes.

BEST MODE FOR CARRYING OUT THE INVENTION

The following Reference Example and Examples illustrate the present invention in further detail In the Reference Example, the compound for use as the starting material in the process of the invention was prepared.

REFERENCE EXAMPLE 1

27.2 g of 4-[(diethoxyphosphoryl)methyl]benzoic acid was suspended in a mixture of 60 ml of dichloromethane and 2 ml of DMF. 13.1 g of thionyl chloride was added, and the resulting mixture was refluxed for 1 hour. After completion of reaction, the reaction mixture was allowed to cool and then slowly added dropwise, with ice-cooling and stirring, to a solution of 18.5 g of 2-(N-methylcarbamoyl)-5-chloroaniline in a mixture of 50 ml of pyridine and 30 ml of dichloromethane. After completion of addition, the resulting mixture was stirred at room temperature for 48 hours. Then, 50 ml of water was added to the reaction mixture to precipitate crystals. The crystals were then collected by filtration, fully washed with water and dried, giving 23.6 g of diethyl 4-{[5-chloro-2-(N-methylcarbamoyl)phenyl]carbamoyl}benzylphosphonate.

Example 1

80g (182.3 mmol) of the compound obtained in Reference Example 1 was dissolved in a mixture of 221 g (2184.0 mmol) of triethylamine and 2000 ml of dichloromethane. 87 g (800.8 mmol) of chlorotrimethyl-silane was slowly added dropwise to the solution with stirring at room temperature. After completion of addition, the resulting mixture was stirred with heating at 40° C. for 17 hours. After completion of reaction, the reaction mixture was concentrated and mixed with 1000 ml of 1N hydrochloric acid. The resulting mixture was subjected to extraction with dichloromethane. The organic layer was dried over magnesium sulfate, and the solvent was distilled off under reduced pressure. Diisopropyl ether was added to the residue for crystallization, and the crystals were collected by filtration. The obtained crude crystals were recrystallized from ethanol and water, giving 88.6 g of the contemplated diethyl 4-(7-chloro-3-methyl-4(3H)-quinazolinon-2-yl)benzylphosphonate.

Examples 2 to 13

The compounds shown in Tables 1 and 2 were prepared by following the procedures of Reference Example 1 and Example 1. The tables show the structures, melting points and yields of the compounds.

In the tables, Me, Et and Ph indicate methyl, ethyl and phenyl groups, respectively.

TABLE 1

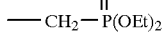

| Ex. | R¹ | R² | R³ | R⁴ | R⁵ | R⁶' | Melting point (° C.) | Yield (%) |
|---|---|---|---|---|---|---|---|---|
| 1 | H | H | Cl | H | Me | —CH₂—P(=O)(OEt)₂ | 142~142.5 | 93 |
| 2 | H | Br | H | H | Et | —CH₂—P(=O)(OEt)₂ | 73~74 | 66 |
| 3 | H | I | H | H | Me | —CH₂—P(=O)(OEt)₂ | 143~144 | 81 |
| 4 | H | H | MeNH—C(=O)— | H | Me | —CH₂—P(=O)(OEt)₂ | 238~239 | 83 |

TABLE 1-continued

[Structure: quinazolin-4(3H)-one with R1 at 5, R2 at 6, R3 at 7, R4 at 8, R5 on N3, and a 2-(4-R6'-phenyl) group]

| Ex. | R$^1$ | R$^2$ | R$^3$ | R$^4$ | R$^5$ | R$^{6'}$ | Melting point (° C.) | Yield (%) |
|---|---|---|---|---|---|---|---|---|
| 5 | H | H | Me—O—C(=O)— | H | Me | —CH$_2$—P(=O)(OEt)$_2$ | 116~117 | 85 |
| 6 | H | H | H | H | Me | H | 135~136 | 63 |
| 7 | H | H | H | H | Ph | H | 157~158 | 78 |
| 8 | H | H | H | H | —CH$_2$—CH=CH$_2$ | H | 81.5~82.5 | 65 |
| 9 | H | H | Cl | H | Me | Me | 125~126 | 68 |
| 10 | H | H | Cl | H | Me | —CH$_2$—P(=O)(Ph)(OEt) | 192~193 | 69 |

TABLE 2

[Structure: quinazolin-4(3H)-one with R1–R4 on benzene ring, R5 on N3, R6 at position 2]

| Ex. | R$^1$ | R$^2$ | R$^3$ | R$^4$ | R$^5$ | R$^6$ | Melting point (° C.) | Yield (%) |
|---|---|---|---|---|---|---|---|---|
| 11 | H | Br | H | H | Ph | CF$_3$ | 146~147 | 73 |
| 12 | H | Cl | H | H | Ph | Me | 183~184.5 | 72 |
| 13 | H | H | Cl | H | Me | —COOEt | 102.5~103.5 | 71 |

Examples 14 to 49

The compounds shown in Tables 3 and 4 can be prepared in high yields by following the procedures of Reference Examples 1 and Example 1.

In the tables, Me, Et and Ph are as defined above, and iPr and Ac indicate isopropyl and acetyl groups, respectively

TABLE 3

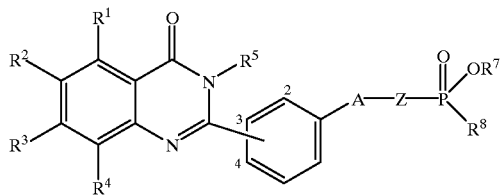

| Ex. | $R^1$ | $R^2$ | $R^3$ | $R^4$ | $R^5$ | $R^7$ | $R^8$ | A | Z | Bonding position | Melting point (° C.) |
|---|---|---|---|---|---|---|---|---|---|---|---|
| 14 | H | Br | Cl | H | Me | Et | OEt | Single bond | $CH_2$ | 4 | 144~145 |
| 15 | H | Br | $NO_2$ | H | Me | Et | OEt | Single bond | $CH_2$ | 4 | 177~178 |
| 16 | H | H | CN | H | Me | Et | OEt | Single bond | $CH_2$ | 4 | 121~122 |
| 17 | H | H | Cl | H | Me | Me | OMe | Single bond | $CH_2$ | 4 | 109~110 |
| 18 | H | H | Cl | H | Me | iPr | OiPr | Single bond | $CH_2$ | 4 | 117~118 |
| 19 | H | Me | H | H | Me | Et | OEt | Single bond | $CH_2$ | 4 | 66.5~67.5 |
| 20 | H | Cl | Cl | H | Me | Et | OEt | Single bond | $CH_2$ | 4 | Oil NMR(1) |
| 21 | H | Cl | Cl | H | Me | Et | OEt | Single bond | $CH_2$ | 4 | Oil NMR(1) |
| 22 | H | Cl | Cl | H | Me | Et | OEt | O | $C_2H_4$ | 4 | Oil NMR(2) |
| 23 | H | H | Cl | H | Me | Et | —$OCH_2$—C$_6$H$_4$—Cl | Single bond | $CH_2$ | 4 | 143~144 |
| 24 | H | H | Cl | H | Me | Et | —$OCH_2$Ph | Single bond | $CH_2$ | 4 | Oil NMR(3) |
| 25 | F | H | H | H | —$CH_2$Ph | Et | OEt | Single bond | $CH_2$ | 4 | 96~97 |
| 26 | H | OMe | H | OMe | Me | Et | OEt | Single bond | $CH_2$ | 4 | 99~100.5 |
| 27 | H | H | —$CF_3$ | H | Me | Et | OEt | Single bond | $CH_2$ | 4 | 51~52 |
| 28 | H | H | H | H | Me | Et | OEt | Single bond | $CH_2$ | 4 | 156~156.5 |
| 29 | H | OMe | OMe | H | —$OCH_2$—C$_6$H$_4$—Br | Et | OEt | Single bond | $CH_2$ | 4 | 103~104 |
| 30 | H | H | Cl | H | —$OCH_2OMe$ | Et | OEt | Single bond | $CH_2$ | 4 | 123~124 |
| 31 | H | H | Cl | H | —$CH_2$—C≡CH | Et | OEt | Single bond | $CH_2$ | 4 | 143~146 |
| 32 | H | H | Cl | H | Me | Me | OMe | Single bond | $CH_2$ | 4 | 109~110 |
| 33 | H | H | $NO_2$ | H | Me | Et | OEt | Single bond | $CH_2$ | 4 | 125.5~126.5 |

| Ex. | $^1$H—NMR (δ: ppm) [CDCl$_3$] |
|---|---|
| 21 | 1.18 (6H, dt, J=4, 7) 3.08 (1H, dd, J=22, 15) 3.44 (3H, s), 3.67 (1H, dd, J=22, 15) |

TABLE 3-continued

|    |    |
|----|----|
| 22 | 3.90–4.02 (4H, m), 7.32–7.59 (5H, m) 7.69 (1H, d, J=2), 8.28 (1H, d, J=9) 1.37 (6H, t, J=7) 2.35 (2H, dt, J=19, 7) 3.52 (3H, s), 4.11–4.20 (4H, m) 4.27–4.37 (2H, m), 7.04 (2H, d, J=9) 7.43 (1H, dd, J=8, 2), 7.53 (2H, d, J=9) 7.71 (1H, d, J=2), 8.24 (1H, d, J=8) |
| 23 | 1.25 (3H, t, J=7), 3.23 (2H, d, J=22) 3.47 (3H, s), 3.94–4.15 (2H, m) 5.04 (2H, d, J=9), 7.35–7.52 (10H, m) 7.71 (1H, d, J=2), 8.23 (1H, d, J=9) |

TABLE 4

| Ex. | R¹ | R² | R³ | R⁴ | R⁵ | R⁶ | Melting point (° C.) |
|-----|----|----|----|----|----|----|----|
| 34 | H | Br | H | H | Ph | —COOEt | 164.5~165.5 |
| 35 | H | Br | H | H | 3,4,5-(OMe)₃-C₆H₂ | Me | 217~218.5 |
| 36 | H | I  | H | H | Ph | Me | 156~157 |
| 37 | H | NO₂ | H | H | Ph | Me | 200.5~222.5 |
| 38 | H | Br | H | H | 4-Cl-C₆H₄ | Me | 155~156.5 |
| 39 | H | H  | H | H | 2-Me-C₆H₄ | Me | 116.5~117.5 |
| 40 | H | Cl | H | Cl | Ph | Me | 191.5~192.5 |
| 41 | H | H  | Cl | Cl | Ph | Me | 238~239.5 |
| 42 | H | Cl | Cl | Cl | Ph | Me | 216.5~217.5 |
| 43 | Cl | Cl | Cl | H | Ph | Me | 191.5~193 |
| 44 | H | H  | H | H | Ph | Me | 250 or above |
| 45 | H | AcO | H | H | Ph | Me | 191.5~192.5 |
| 46 | H | H  | Cl | H | Ph | Me | 173~174 |
| 47 | H | Br | H | H | Ph | Me | 180.5~182 |
| 48 | H | H  | Cl | H | Me | —CH₂—Cl | 163~164.5 |
| 49 | H | H  | Cl | H | Me | CF₃ | 120~122 |

We claim:

1. A process for preparing a quinazolin-4-one derivative, the process comprising reacting, in the presence of a base, a trialkylsilyl halide with a compound represented by the formula

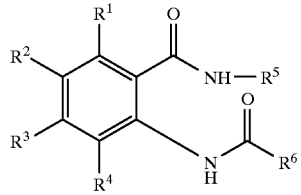

wherein $R^1$, $R^2$, $R^3$ and $R^4$ are the same or different and each represent a hydrogen atom, a lower alkyl group, a halogen atom, a nitro group, a lower alkoxy group, a cyano group, an N-lower alkylcarbamoyl group, a lower alkoxycarbonyl group, a lower alkanoyloxy group or a halogen-substituted lower alkyl group; $R^5$ is a phenyl group which may have 1 to 3 substituents each selected from a lower alkyl group, a lower alkoxy group or a halogen atom, a lower alkyl group, a phenyl-lower alkyl group which may have a halogen atom as a substituent on the phenyl ring, a lower alkenyl group, a lower alkoxy-lower alkyl group or a lower alkynyl group; $R^6$ is a lower alkyl group, a halogen-substituted lower alkyl group, a lower alkoxycarbonyl group or a phenyl group which may have, as a substituent, a lower alkyl group or a group of the formula

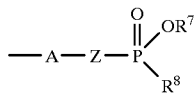

wherein A is an oxygen atom or a single bond, Z is a lower alkylene group, $R^7$ is a lower alkyl group and $R^8$ is a lower alkoxy group, a phenyl group or a phenyl-lower alkoxy group which may have a halogen atom on the phenyl ring;

to produce the quinazolin-4-one derivative being represented by the formula

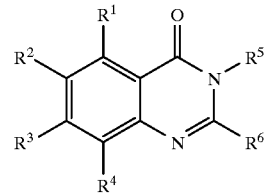

wherein $R^1$, $R^2$, $R^3$, $R^4$, $R^5$ and $R^6$ are as defined above.

2. A process according to claim 1 wherein the base is a tertiary amine.

3. A process according to claim 1 or 2 wherein the trialkylsilyl halide is a chlorotrialkylsilane.

4. A process according to claim 1 or 2 wherein the base and trialkylsilyl halide are used each in an amount of 3 to 20 equivalents.

5. A process according to claim 1 or 2 wherein the reaction temperature is in the range of 0 to 100° C.

6. A process according to claim 3 wherein the base and trialkylsilyl halide are used each in an amount of 3 to 20 equivalents.

7. A process according to claim 3, wherein the reaction temperature is in the range of 0 to 100° C.

8. A process according to claim 4, wherein the reaction temperature is in the range of 0 to 100° C.

* * * * *